United States Patent [19]

Ryder

[11] 4,242,304
[45] Dec. 30, 1980

[54] CONTACT LENS DISINFECTOR WITH TEMPERATURE INDICATOR

[75] Inventor: Francis E. Ryder, Arab, Ala.

[73] Assignee: Ryder International Corporation, Arab, Ala.

[21] Appl. No.: 51,123

[22] Filed: Jun. 22, 1979

[51] Int. Cl.³ .................... G01D 11/26; A01L 2/100; G01K 5/62
[52] U.S. Cl. .................... 422/119; 422/199; 422/300; 116/221; 73/363.5; 40/450
[58] Field of Search ............ 422/292, 119, 199, 300; 116/221; 73/363.5, 363.7; 206/305, 306; 296/169 R, 169 A; 219/438, 439, 441, 510, 512, 521; 40/447, 450, 449

[56] References Cited

U.S. PATENT DOCUMENTS

| | | | |
|---|---|---|---|
| 1,816,112 | 7/1931 | Deisch | 116/221 |
| 3,837,102 | 9/1974 | Golay | 40/450 |
| 3,983,362 | 9/1976 | Hoogesteger et al. | 422/300 |
| 4,164,824 | 8/1979 | Nidelkoff | 40/450 |

Primary Examiner—S. Leon Bashore
Assistant Examiner—Chris Konkol
Attorney, Agent, or Firm—Trexler, Wolters, Bushnell & Fosse, Ltd.

[57] ABSTRACT

A contact lens disinfector unit (10) includes a housing, heating means arranged to heat the contact lenses and the associated lens case (21) to a disinfecting temperature and for thereafter terminating the application of heat to allow the contact lenses to cool, and temperature indicating means (30) for indicating if the lens case is cool enough for safe handling. The temperature indicating means includes a viewing window (17) having opaque portions (38) and transparent portions (37). The transparent portions are arranged to define a temperature indicia. The temperature indicator also includes a plate (35) which has indicia thereon corresponding to the temperature indicia and a surrounding opaque background. The plate is slidable with respect to the viewing window between two positions, one of which indicates that the lens case is too hot to handle, and the other of which indicates that the lens case is cool enough to handle.

3 Claims, 6 Drawing Figures

CONTACT LENS DISINFECTOR WITH TEMPERATURE INDICATOR

BACKGROUND OF THE INVENTION

This invention is to a contact lens disinfector unit with an improved temperature indicator.

Prior art disinfector units of the type that include a cast that holds the contact lenses and a disinfecting solution have generally controlled the application of electric current to the heating block (which heats the lens case and solution) with a thermocouple switch. The thermocouple, after detecting a predetermined temperature of the heating block, breaks the switch contact for shutting off the electric current. Wired in series with the switch is usually a light bulb. The light bulb lights up when the switch is closed and the electric current is being applied to the heating block and is turned off when the thermocouple opens the switch to terminate the application of the electric current to the heating block. Because of this arrangement, the user does not know just when the contact lens case has cooled sufficiently to be safely removed. The user may, therefore, either attempt to remove the lens case too soon, resulting in possible injury, or wait an unnecessarily long time after the light is extinguished to be assured that the lens case is cool enough. An object of the present invention to provide a new and improved contact lens disinfector unit which includes an improved arrangement for indicating when the contact lens case has cooled sufficiently for safe removal.

The present invention provides a contact lens disinfector unit for sterilizing contact lenses contained within a lens case. The contact lens disinfector unit includes a housing, heating means arranged to heat the contact lenses to a disinfecting temperature and for thereafter terminating the application of heat to allow the contact lenses to cool, and temperature indicating means for indicating first and second temperatures of the heating means. The temperature indicator includes a viewing window having opaque portions and transparent portions. The transparent portions are arranged to define a temperature indicia. The temperature indicator also includes a plate below the viewing window having an upper surface with an indicia thereon corresponding to the temperature indicia and a surrounding opaque background. The plate is slidable with respect to the viewing window between a first position whereat the plate indicia is in registration with the viewing window transparent portions and a second position whereat the plate background underlies the viewing window transparent portions for removing the temperature indicia from view. The temperature indicator further includes an actuating means for moving the plate between the first and second positions responsive to first and second temperatures of the heating means.

DESCRIPTION OF THE PREFERRED EMBODIMENT

Figure 1:
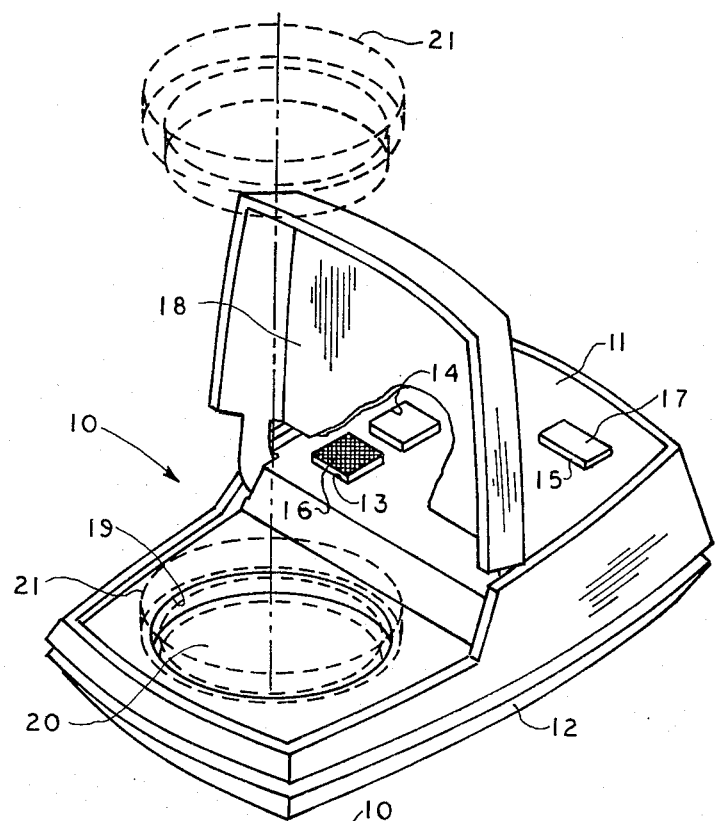
FIG. 1 is a perspective view of a contact lens disinfector unit embodying the present invention showing its hinged cover in a raised position and with a contact lens case (in dashed lines) shown both in an exploded position relative to the disinfector unit and also in an operative position within the unit.

Referring now to FIG. 1, a disinfector unit 10 includes a housing with a top cover section 11 and a bottom section 12. The top cover section has openings 13, 14 and 15. In the first opening 13 there is an activator button 16 mechanically coupled to a thermocouple switch 2. When button 16 is depressed a disinfecting cycle is initiated. The second opening 14 is disposed over an internal light bulb 27 which lights when the thermocouple 22 is closed for indicating that the unit 10 is in the heating mode. The light bulb 27 shuts off when the thermocouple switch 22 opens upon reaching a disinfecting temperature. Within the opening 15 there is a viewing window 17 through which the user may view a temperature indicating indicia in accordance with the present invention. By viewing through the viewing window 17, the user may be informed whether the contact lens case 21 is too hot to be removed from the disinfector unit or that the contact lens case is sufficiently cool to enable safe removal of the lens case from the disinfector unit.

The top cover section 11 includes a hinged lid portion 18 which is shown in a raised position in FIG. 1 to permit insertion and removal of the lens case 21 into and from the housing. In addition, the top cover 11 includes a circular recess 19 which communicates with the upper surface of a heating block 20 that is within the unit 10. The recess 19 is dimensioned for receiving the lens case 21. The lens case 21 may be of known construction and including bottom portion 21a removably engaged with an upper portion 21b and otherwise designed to receive a pair of lenses and a quantity of disinfecting solution. Preferably, the lens case 21 and the recess 19 are dimensioned such that the bottom surface of the lens case makes surface-to-surface contact with the upper surface of the heating block 20. During the disinfecting cycle, the heating block 20 provides sufficient heat transfer to the lens case 21 so as to heat the contact lenses and the solution to a disinfecting temperature sufficient to kill pathogenic bacteria on the lenses.

Figure 2:
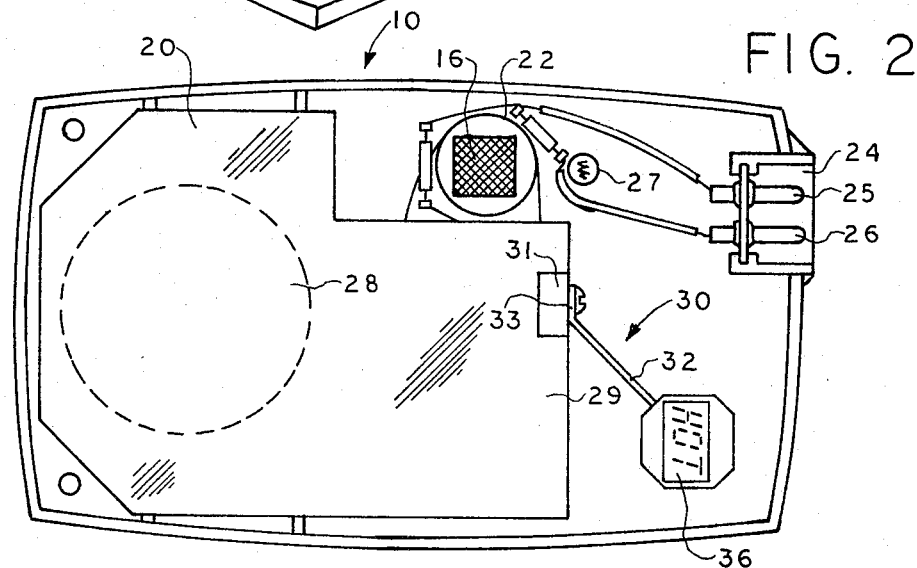
FIG. 2 is a top plan view of the interior of the disinfector unit of FIG. 1, the top or cover portion of the unit housing having been removed.

Referring now to FIG. 2, the disinfector unit 10 includes the aforementioned heating block 20, the thermocouple switch 22 with its activator or reset button 16 that extends through the opening 13, and a power supply circuit for a resistive heating element (not shown). The power supply circuit is adapted to be connected to an electric power source by pins 25 and 26 of a connector 24. When the button 16 is depressed the switch 22 closes to energize the resistive heater and the lamp 27. When the correct disinfecting temperature has been reached, the switch 22 opens, the lamp 27 goes out, and current to the resistive heater is interrupted.

The heating block 20 includes a surface portion 28 shown in dashed lines in FIG. 2 which engages the undersurface of the lens case 21 during the heating cycle. The heating block includes a rearward portion 29 which terminates in an upstanding post 31 to which an indicating arrangement 30 is operatively connected. The heating block 20 is in contact with the resistive heating element referred to previously. Due to the surface-to-surface contact with the case 21 the block 29 applies heat evenly thereto so as to raise the temperature of the disinfecting solution to that required for disinfecting of the contact lenses. The circuit providing power to the resistive heater under control of the thermocouple 22 is of a type well known in the art and need not be described in further detail herein.

Referring to FIGS. 3-6 the temperature indicating arrangement 30 includes a temperature sensitive member 32 in the form of a bi-metallic strip which has one end 33 affixed to the upstanding portion 31 of the heating block 20 and the other end 34 free to move laterally in first and second directions. The end 34 will move in a first direction as the temperature of the heating block 20 and lens case 21 rises and in a second direction as the heating blocking and lens case cools. The reciprocal movement of the bi-metallic strip 32 is used to impart relative movement to a temperature indicia carried by a planar slide member 35. The position of the slide and hence the position of the temperature indicia will indicate whether or not the lens case is cool enough for handling.

Figure 3:
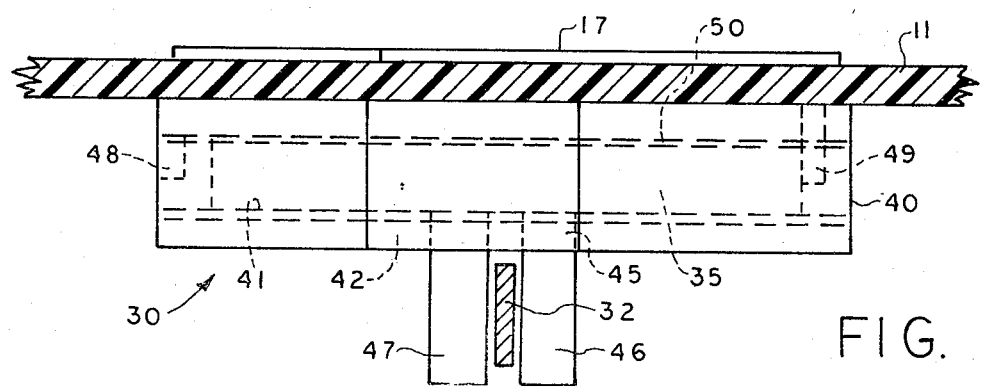
FIG. 3 is a partial, cross-sectional view taken generally along lines 3—3 of FIG. 5 illustrating the temperature indicating arrangement of the present invention.
Figure 4:
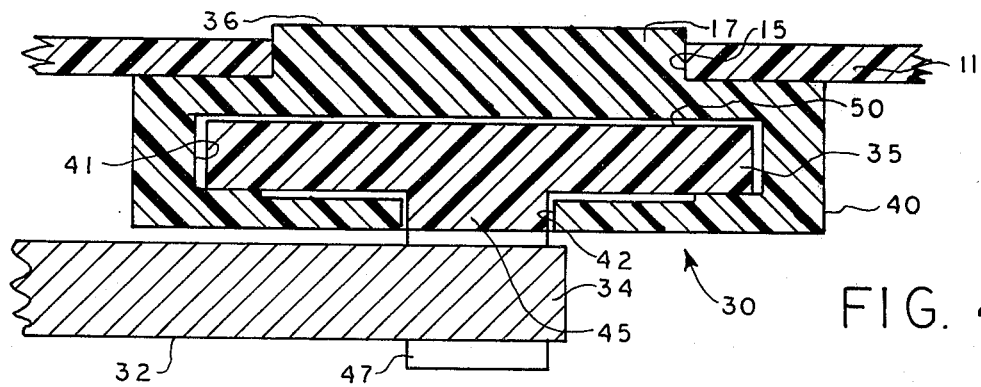
FIG. 4 is a cross-sectional view taken generally along lines 4—4 of FIG. 5.
Figure 5:
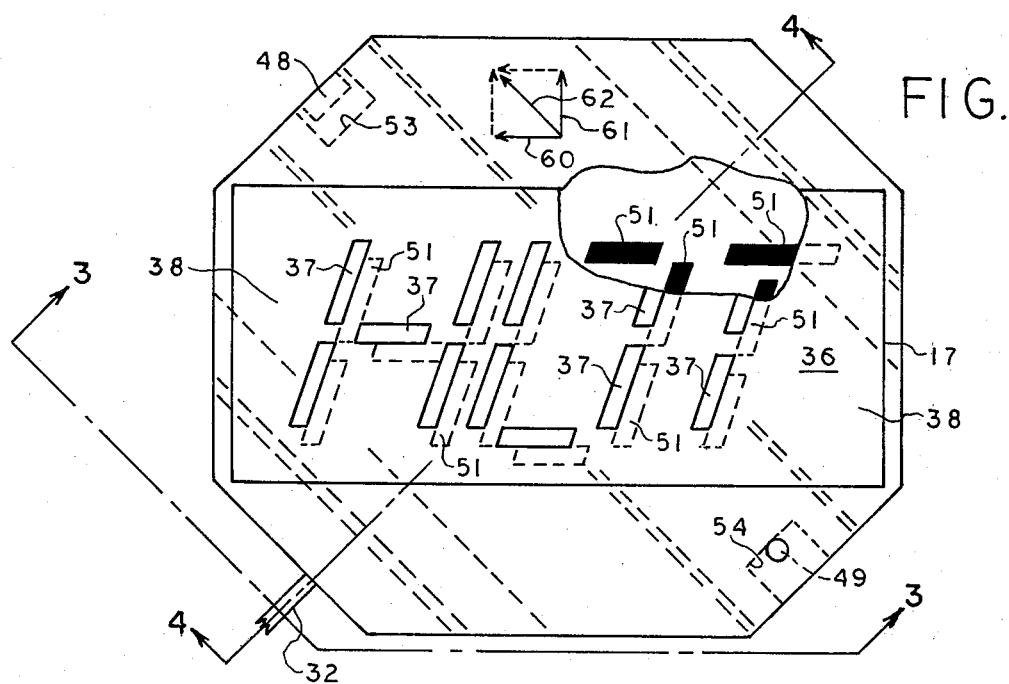
FIG. 5 is a top view of the unit, with portions cut away of a temperature indicator embodying the present invention, showing the temperature indicator in one of its operative conditions.

Referring specifically to FIGS. 3, 4, and 5, the viewing window 17 includes a portion which extends through the opening 15 of the top cover section 11. On the upper surface 36 of the viewing window 17 there are transparent portions 37 and a surrounding opaque background 38. The transparent portions 37 are arranged to define a temperature indicia. Preferably the transparent portions 37 are arranged to form a segmented, multiple character indicia defining the word "HOT".

The viewing window 17 includes a lower body portion 40 which is arranged to form an internal guide track 41 for guiding the relative movement of the plate 35 between first and second positions. The body portion 40 of the viewing window 17 includes a slot 42 through which a downward extension 45 of plate 35 projects. The downward extension 45 terminates in a pair of spaced apart bifurcated members 46 and 47 which receive the second end 34 of the bi-metallic strip therebetween.

The bi-metallic strip 32 moves the plate 35 between a second position and a first position relative to the viewing window 17. The plate 35 includes on its upper surface 50 an indicia corresponding in shape and position to the temperature indicia defined by the transparent portions 37 of the viewing window 17. As can be seen in FIG. 5, the temperature indicia carried by the upper surface 50 of the plate 35 takes the form of a segmented, multiple character indicia comprising the word "HOT". The indicia carried by the plate 35 therefore includes a plurality of segments 51 which are surrounded by a background having a similar color or visual characteristic as the opaque portion 38 of the viewing window; however, the segments 51 are of a different visual characteristic than the background area of the plate 35 and the opaque portion 38 of the viewing window. For example, the segments 51 may be red in color while the plate background and viewing window opaque portions may be black.

In FIG. 5, the viewing window and the plate 35 are shown in a second position in which the plate background underlies the viewing window transparent portions 37 so as to render the transparent portions indiscernable. Hence, when in this operative condition, the temperature indicator viewing window will appear to be totally black. This may correspond, for example, to the heating block and lens case being at a cool temperature to inform the user that the lens case may be safely removed from the disinfector unit.

Figure 6:
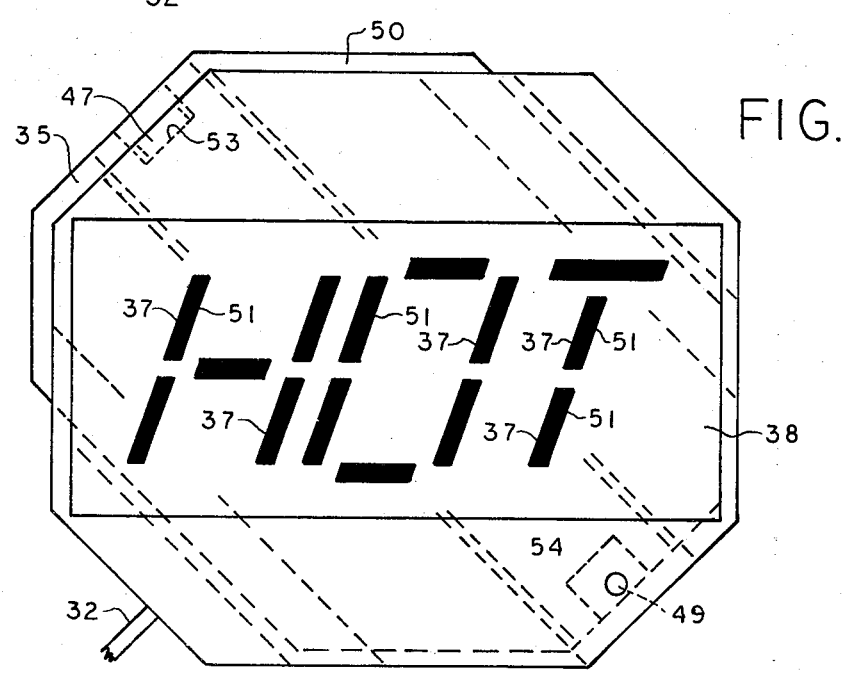
FIG. 6 is a top view, similar to FIG. 5, illustrating the temperature indicator in another operative condition.

During the disinfecting cycle, as the heating block and lens case are raised in temperature, the heating block and lens case will reach a temperature which is too hot to facilitate safe removal of the lens case from the disinfecting unit. In order to provide an indication as to the hot condition of the lens case, as the heating block heats, the bi-metallic strip 32 will move (blend) laterally from a second position to a first position so as to cause the plate 35 to slide within the guide track 41 of the viewing window 17. The plate 35 will continue to slide within the guide track until the plate 35 and viewing window 17 reach their first relative position. In FIG. 5, it is shown that the guide plate 35 includes a cutout portion 53 which is spaced from a downwardly extending stop 48 of the viewing window. When the cutout portion 53 engages the stop 48 as the bi-metallic strip causes the plate 35 to move in the second direction, the indicia segments 51 of the plate will be in registration with the viewing window transparent portions 37 as shown in FIG. 6. This renders the temperature indicia defining by the transparent portions 37 and the segments 51 in register to be viewable through the viewing window. As a result, the temperature indicia word "HOT" will appear in the viewing window in a segmented, multiple character form, to inform the user that the lens case is too hot to be safely removed from the disinfector unit.

The stop comprising the stop member 48 and cutout portion 53 assures that the indicia segments 51 will remain in registration with the transparent portions 37 of the viewing window 17 throughout a range of temperatures of the heating block and lens case considered to be too hot for safe removal of the lens case from the disinfector unit. Also, the guide track 41 guides the plate 35 for lateral sliding movement somewhat diagonally across the viewing window 17. More specifically, the guide track 41 is arranged to guide the plate 35 for movement in first and second component directions which are prependicular to one one another as indicated by the arrows 60 and 61 simultaneously to cause the plate 35 to move at a resultant angle of 45° as indicated by the arrow 62. Because of this angular movement of the plate indicia with respect to the transparent portions 37 of the viewing window, the temperature indicia carried by the plate is caused to be rendered viewable through the viewing window as a result of a rather short distance of travel of the plate 35 and thus in a relatively short period of time. As a result, a positive and readily discernable indication is thus provided by the temperature indicating arrangement of the present invention.

Although a segmented character display has been shown, the display of course could take a non-segmented form. However, the segmented display is considered preferable inasmuch as, as can be seen in FIG. 5, when the viewing window and plate are at their second relative position, no portion of the indicia segments 51 are viewable through the viewing window transparent portions 37. Furthermore, to be assured of the limited travel required by the plate 35 in moving to the first position, the viewing window includes a stop pin 49 against which a second cutout portion 54 of the plate 35 abuts. The pin 49 and cutout portion 54 are preferably arranged to abut when the indicia segments 51 are just removed from view through the transparent segments 37 of the viewing window 17.

The invention is claimed as follows:

1. A disinfector unit for contact lenses comprising, a housing, heating means arranged for heating the contact lenses to a desired temperature and indicating means for providing a visual message for impression to the user that the unit is in a selected temperature condition, said indicating means comprising a generally opaque viewing window including a plurality of longitudinal and transverse transparent portions arranged to define a series of segmented characters providing a visual, word message, a plate having an upper surface including an opaque background corresponding to the opaque portions of said viewing window and a series of longitudinal and transverse portions of a selected color which correspond in size, shape and arrangement to the transparent portions of said viewing window, means mounting said plate below said viewing window for slidable movement in a diagonal direction with respect to said window and the transparent portions thereof, and temperature responsive actuator means operatively coupled with said plate for movement of said plate between a first and a second position in response to the changes of temperature of said unit, such that when said plate is moved to said first position, said longitudinal and transverse colored portions on said plate align with the corresponding longitudinal and transverse transparent portions of said window, thereby providing a visual word message display to the user, with movement of said plate diagonally to said second position producing total misalignment of said longitudinal and transverse colored portions with respect to said transparent portions, such that only the opaque portion of said plate is aligned with said transparent portion, thereby totally obliterating said work message.

2. A disinfector unit as defined in claim 1, wherein said actuator means comprises a bimetallic strip having a first end connected to said heating means and a second end coupled to said plate.

3. A disinfector unit as defined in claim 2 further including a guide track for guiding the diagonal movement of said plate.

* * * * *